United States Patent
Römisch et al.

(10) Patent No.: US 6,514,940 B2
(45) Date of Patent: *Feb. 4, 2003

(54) STABILIZED ANTITHROMBIN III PREPARATION

(75) Inventors: Jürgen Römisch, Marburg (DE); Harald Stauss, Dautphetal (DE)

(73) Assignee: Aventis Behring GmbH, Marburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/456,991

(22) Filed: Dec. 7, 1999

(65) Prior Publication Data

US 2002/0172933 A1 Nov. 21, 2002

(30) Foreign Application Priority Data

Dec. 8, 1998 (DE) .......................... 198 56 443

(51) Int. Cl.⁷ ............................................... A61K 38/36
(52) U.S. Cl. ......................................................... 514/12
(58) Field of Search ............................................. 514/12

(56) References Cited

U.S. PATENT DOCUMENTS

| 4,297,344 A | | 10/1981 | Schwinn et al. | |
|---|---|---|---|---|
| 4,340,589 A | | 7/1982 | Uemura et al. | |
| 4,579,735 A | * | 4/1986 | Heimburger et al. | 424/101 |
| 4,623,717 A | | 11/1986 | Fernandes et al. | |
| 4,687,664 A | * | 8/1987 | Philapitsch et al. | 424/85 |
| 4,876,241 A | * | 10/1989 | Feldman et al. | 514/2 |
| 5,989,593 A | * | 11/1999 | Ideno et al. | 424/529 |

FOREIGN PATENT DOCUMENTS

EP 0 018 561 11/1980

OTHER PUBLICATIONS

Busby, Thomas F. and Ingham, Kenneth C., "Thermal Stabilization of Antithrombin III by Sugars and Sugar Derivatives and the Effects of Nonenzymatic Glycosylation," *Biochimica et Biophysica Acta*, vol. 799, 80–89 (1984).
International Search Report, dated Apr. 17, 2000.

* cited by examiner

*Primary Examiner*—Jean C. Witz
(74) *Attorney, Agent, or Firm*—Finnegan, Henderson, Farabow, Garrett and Dunner, L.L.P.

(57) ABSTRACT

A stabilized antithrombin III preparation is described which is protected against a loss of action during pasteurization by the addition of stabilizers which consist of one or more saccharides in a mixture with more than 0.5 mol/l of one or more amino acids from the group consisting of arginine, lysine, histidine, phenylalanine, tryptophan, tyrosine, aspartic acid and its salts or glutamic acid and its salts, it also being possible to additionally add glycine or glutamine to each of these amino acids.

12 Claims, No Drawings

STABILIZED ANTITHROMBIN III PREPARATION

The invention relates to a stabilized antithrombin III preparation which is protected against a loss of action during pasteurization by the addition of stabilizers, and to a process for virus inactivation of an antithrombin III preparation of this type.

Antithrombin III (ATIII) is one of the most important plasmatic inhibitors. ATIII belongs to the family of serine protease inhibitors, which with their "target proteases" enter into a complex approximating the covalent bond. This complex is very stable under physiological conditions and as a rule is rapidly eliminated from the blood circulation. The reaction between ATIII and the protease is drastically accelerated by heparin, the ATIII undergoing a slight change in conformation after association with the glycosaminoglycan and thus being able to enter into an accelerated reaction with the protease. Physiologically, these processes play a role, particularly on cell surfaces which contain glycosaminoglycans, e.g. of the heparin sulfate type, and thus represent a barrier of the cells and tissue against excessive proteolytic activity. In addition, however, plasmatic coagulation, and its regulation, is also of great importance.

The regulatory function of this inhibitor is particularly clear when the ATIII plasma levels fall, as is observed in many illnesses and particularly drastically, for example, in the case of disseminated intravascular coagulation (DIC). Even a shortfall of 70% of the corresponding plasma concentration is associated with a drastic increase in the probability of mortality. A predominance of clotting processes frequently leads to thrombotic occlusions of vessels and thus to organ failure. Correspondingly, administration of ATIII concentrates from human plasma has proven very helpful, particularly in cases of inherited and acquired deficiency states.

Patients who suffer from inherited or acquired ATIII deficiency are at present treated by substitution of concentrates obtained from human plasma. In addition to the effectiveness of these concentrates, safety with respect to the potential risk of transfer of infectious diseases must particularly be guaranteed. In addition to virus inactivation processes, such as treatment with detergents, e.g. according to the SD (solvent/detergent) method, the heat inactivation of viruses at 60° C., which has already been used in the 1940s for albumin, is also suitable for this purpose. In general, proteins are treated at 60° C. for up to 10 hours during pasteurization. This high temperature, however, can lead to denaturation of the proteins, which results in losses in activity and yield. In the case of ATIII, this is reflected in the loss of the heparin-binding properties of a specific protein fraction. This ATIII fraction is no longer measurable in a heparin cofactor test and is seen in two-dimensional immunoelectrophoresis as a separate peak, which can be clearly differentiated from the heparin-binding fraction.

The changes, which can mostly be attributed to conformational changes in the protein, are counteracted by addition of stabilizers to the solution to be heated. To achieve optimum protection of proteins of this type, the stabilizers employed for this must be exactly suited to each protein both in their composition and in the quantitative proportions of the individual constituents of the stabilizer mixture. Accordingly, U.S. Pat. No. 4,297,344 discloses a specific stabilizer mixture for ATIII which is used in pasteurization processes. In this patent, ATIII is mixed in aqueous solution with a carbohydrate such as sucrose and at least one amino acid from the series consisting of glycine, α- and β-alanine, hydroxyproline, glutamine and α-, β- or γ-butyric acid. However, completely satisfactory stabilization of ATIII cannot be thus achieved, as the heparin-nonbinding fraction is over 12% after pasteurization.

It has now been found that ATIII can be significantly more effectively protected against a loss of action during pasteurization if either one or more saccharides in a higher concentration (>1 g/ml) or one or more saccharides in combination with one or more amino acids from the group consisting of arginine, lysine, histidine, phenylalanine, tryptophan, tyrosine, aspartic acid and its salts and also glutamic acid and its salts is selected as a stabilizer. One or more of these amino acids can also be combined with glycine and/ or glutamine here.

The stabilizers are normally employed in a buffer solution, e.g. a citrate solution.

The saccharide employed can be a monosaccharide, a disaccharide or an oligosaccharide in an amount of at least 0.5 g/ml. However, a value of over 1.0 g/ml is preferred, at the same time a pH of 6.0 to 9.5, preferably of 7.0 to 8.5, being used.

The abovementioned amino acids are employed on their own or in combination in an amount of at least 0.1 mol/l, but preferably in an amount of more than 0.5 mol/l. Combinations of one or more sugars in a concentration of more than 1.5 g/ml and one or more amino acids in concentrations of more than 0.1 mol/l in each case are particularly preferred here. The combination of a sugar in an amount of more than 1.5 g/ml and one or more of the abovementioned amino acids with glycine and/or glutamine, which are all used in concentrations of over 0.2 ml in each case, is also particularly preferred. Ammonium sulfate can be added in combination with the abovementioned stabilizers up to a final concentration of 15%.

For virus inactivation, the solution of ATIII stabilized in this way is heated at 40 to 95° C., preferably at 50 to 70° C., for 5 to 50 hours, preferably 8 to 20 hours. However, virus inactivation at 55 to 65° C., is most favorable.

The preparation processes for the ATIII concentrates, such as chromatographic processes by means of immobilized heparin, are known to the person skilled in the art. The process according to the invention for virus inactivation is in general applied to ATIII obtained from plasma and is dependent on the plasma fraction which is selected as a starting material for the further purification of the ATIII. The invention can likewise also be applied to recombinantly prepared or transgenic ATIII.

The stabilization described can also be used in other virus inactivation processes.

The invention is illustrated by the following examples:

EXAMPLE 1

5 to 10 ml each of a solution which contained ATIII in a concentration of approximately 200 IU/ml were mixed with sucrose alone and in combination with one or more amino acids and incubated at 60° C., for 10 hours. The nativity of the ATIII in the sense of the heparin-binding properties was then determined by two-dimensional immuno-electrophoresis. For this, an electrophoresis of the protein solution was carried out in the presence of heparin. The heparin-binding molecules became more strongly negatively charged as a result and migrated correspondingly more rapidly in the electrical field. An agarose gel with addition of a polyclonal antibody against ATIII was then poured onto the first gel and the electrical field was applied at a right angle to the direction of the first run. In regions of equimolar ratios of ATIII to antibody, a precipitation reaction took place. After soaking the gel, the precipitation line was rendered clearly visible in the form of a curve or of a peak by staining, for example, with Coomassie Blue. Quantification of the heparin-binding or-nonbinding fraction was carried out by drawing the base line with the aid of a scanner and integration of the peak areas, whose sum was set equal to 100%. The corresponding peaks were related to this and the appropriate fraction was expressed in percent. The detection limit of the method is 3% of heparin-nonbinding fraction.

Several lots were tested in each case, the ATIII solution before pasteurization always being included as a control.

The following batches were pasteurized and evaluated as described. The results are shown as mean values of 2 to 5 lots. Experiments Nos. 1, 2, 3A and 3B represent the prior art. Experiments 4, 5, 6, 7 and 8 show that in the case of an antithrombin III preparation stabilized according to the invention the heparin-nonbinding fraction is between approximately 3 and 4%.

| No. | Sucrose (g/ml) | Amino acids (mol/l) | Heparin-nonbinding fraction (%) |
|---|---|---|---|
| 1 | before pasteurization | | <3 |
| 2 | 0.5 | ... | >20 |
| 3A | 1.0 | glycine (2 mol/l) | 12.8 |
| 3B | 1.0 | glycine (2 mol/l) (arginine (2 mol/l)/ glutamate (2 mol/l) were added only after pasteurization) | 12.6 |
| 4 | 1.75 | glycine (2 mol/l)/ glutamate (2 mol/l) | <3.5 |
| 5 | 1.75 | glycine (2 mol/l)/ glutamate (2 mol/l) | <3 |
| 6 | 1.75 | arginine (2 mol/l) | 4.3 |
| 7 | 1.75 | lysine (2 mol/l) | 3.9 |
| 8 | 1.75 | glutamate (1 and 2 mol/l) | <3 |

Result:

As expected, the respective batch before pasteurization (No. 1) in each se contained <3% of heparin-nonbinding fraction ATIII. After heating, batches without, or with very low amounts of, stabilizer showed >20% of the nonbinding protein (No. 2).

The mixtures with glycine/glutamate (No. 4) with on average <3.5% and particularly with glycine/glutamate/arginine (No. 5) with <3% showed very effective stabilizing actions. The combinations of sucrose, for example, with arginine or lysine (No. 6,7) have also turned out to be advantageous. Even glutamate on its own brought about very effective stabilization (No. 8).

To investigate whether the stabilizers added, particularly the amino acids glutamate and arginine, affected the electrophoretic running behavior on their own, these were added (No. 3B) to the sucrose/glycine mixture only after pasteurization and compared with the control (3A). It was demonstrated that these additives had no significant influence on the electrophoresis.

EXAMPLE 2

The dependence of the stabilization on the sugar concentration was investigated according to the experimental procedure in Example 1.

| No. | Sucrose (g/ml) | Amino acids (mol/l) | Heparin-nonbinding fraction (%) |
|---|---|---|---|
| 1 | before pasteurization | | <3 |
| 2 | 0.5 | ... | >20 |
| 3A | 1.0 | glycine (2 mol/l) glutamate | 6.8 |
| 3B | 1.0 | glycine (2 mol/l) | 12.8 |
| 3C | 1.75 | glycine (2 mol/l) | 5.4 |
| 4A | 0.5 | glutamate (1 mol/l)/ arginine (2 mol/l) | 14.1 |
| 4B | 1.0 | glutamate (1 mol/l)/ arginine (2 mol/l) | 6.4 |
| 4C | 1.75 | glutamate (1 mol/l)/ arginine (2 mol/l) | <3 |

Result:

Both the batches 3B and C and also 4A to C show that the increase in the sugar content afforded an important contribution to the stabilization. The additionally stabilizing effect of glutamate/arginine (4B) or glutamate (3A) or compared with the batches with glycine (3A versus 3B) at a sucrose concentration of only 1 mol/l was also clear.

What is claimed is:

1. A pasteurized and liquid antithrombin III preparation protected against a loss of activity during pasteurization, comprising antithrombin III, and a stabilizer comprising:

a) one or more saccharides in a concentration of at least 1.5 g/ml; and b) one or more amino acids selected from the group consisting of glycine, arginine, lysine, histidine, phenylalanine, tryptophan, tyrosine, aspartic acid, an aspartic acid salt, glutamic acid, and a glutamic acid salt;

wherein the heparin-nonbinding fraction of said antithrombin III is less than 12%.

2. The pasteurized and liquid antithrombin III preparation as claimed in claim 1, wherein the stabilizer additionally contains at least one of glycine or glutamine.

3. The pasteurized and liquid antithrombin III preparation as claimed in claim 1, wherein said one or more saccharides are selected from at least one of a monosaccharide, a disaccharide, and an oligosaccharide.

4. The pasteurized and liquid antithrombin III preparation as claimed in claim 1, wherein said one or more saccharides are in an amount of more than 1.5 g/ml.

5. The pasteurized and liquid antithrombin III preparation as claimed in claim 1, which contains one or more amino acids in an amount of at least 0.1 mol/l.

6. The pasteurized and liquid antithrombin III preparation as claimed in claim 1, which additionally contains up to 15% w/v of ammonium sulfate.

7. A process for preparing the pasteurized and liquid antithrombin III preparation as claimed in claim 1, which comprises subjecting a stabilized antithrombin III preparation to heat treatment at 40 to 95° C. over a period of time of 5 to 50 hours.

8. The process for preparing the pasteurized and liquid antithrombin III preparation as claimed in claim 3, which comprises subjecting a stabilized antithrombin III preparation to heat treatment at 40 to 95° C. over a period of time of 5 to 50 hours.

9. The process for preparing the pasteurized and liquid antithrombin III preparation as claimed in claim 4, which comprises subjecting a stabilized antithrombin III preparation to heat treatment at 40 to 95° C. over a period of time of 5 to 50 hours.

10. The process for preparing the pasteurized and liquid antithrombin III preparation as claimed in claim 5, which comprises subjecting a stabilized antithrombin III preparation to heat treatment at 40 to 95° C. over a period of time of 5 to 50 hours.

11. The process for preparing the pasteurized and liquid antithrombin III preparation as claimed in claim 6, which comprises subjecting a stabilized antithrombin III preparation to heat treatment at 40 to 95° C. over a period of time of 5 to 50 hours.

12. The process for preparing the pasteurized and liquid antithrombin III preparation as claimed in claim 2, which comprises subjecting a stabilized antithrombin III preparation to heat treatment at 40 to 95° C. over a period of time of 5 to 50 hours.

* * * * *